(12) United States Patent
Hong (10) Patent No.: US 11,854,692 B2
(45) Date of Patent: Dec. 26, 2023

(54) CLOUD-BASED API SPEC MANAGEMENT METHOD FOR SIMULTANEOUSLY INTERCONNECTING PLURALITIES OF HOSPITAL SERVERS AND CONSORTIUM SERVERS

(71) Applicant: LEMONHEALTHCARE LTD, Seoul (KR)

(72) Inventor: Byung Jin Hong, Seoul (KR)

(73) Assignee: LEMONHEALTHCARE LTD, Seoul (KR)

( * ) Notice: Subject to any disclaimer, the term of this patent is extended or adjusted under 35 U.S.C. 154(b) by 0 days.

(21) Appl. No.: 17/925,710

(22) PCT Filed: Feb. 16, 2021

(86) PCT No.: PCT/KR2021/001956
§ 371 (c)(1),
(2) Date: Nov. 16, 2022

(87) PCT Pub. No.: WO2021/256657
PCT Pub. Date: Dec. 23, 2021

(65) Prior Publication Data
US 2023/0197256 A1  Jun. 22, 2023

(30) Foreign Application Priority Data
Jun. 18, 2020 (KR) .................. 10-2020-0074341

(51) Int. Cl.
*G16H 40/20* (2018.01)
*G16H 50/70* (2018.01)
(Continued)

(52) U.S. Cl.
CPC ............ *G16H 40/20* (2018.01); *G06F 9/547* (2013.01)

(58) Field of Classification Search
CPC ............................... G16H 40/20; G06F 9/547
See application file for complete search history.

(56) References Cited

U.S. PATENT DOCUMENTS

| 11,170,892 B1* | 11/2021 | McKinney, IV | ....... G16H 15/00 |
| 2016/0321400 A1* | 11/2016 | Durrant | ................. A61N 1/3904 |
| 2020/0218637 A1* | 7/2020 | Walters | .................. G06N 3/047 |

FOREIGN PATENT DOCUMENTS

| JP | 2019503017 A | 1/2019 |
| KR | 1020120093560 A | 8/2012 |

(Continued)

*Primary Examiner* — Maroun P Kanaan
(74) *Attorney, Agent, or Firm* — NKL Law; Byungwoong Park (57) ABSTRACT

Proposed is a cloud-based API specification management method for simultaneously interworking multiple hospital servers and consortium servers. In the method, a cloud server may simultaneously inquire a patient number from the multiple hospital servers when a user terminal executes a dedicated application to input personal identification information, the registration confirmation of the patient number is transmitted to the user terminal when the cloud server confirms whether the patient number is registered in an hospital server among the multiple hospital servers, and the user terminal logs in with the patient number, and the cloud server identifies hospital information when it calls the medical treatment service, thus requesting the hospital server to interwork the medical treatment service. Further, the cloud server may merge multiple pieces of patient data and simultaneously requests service interworking from the multiple consortium servers in response to the service selected by the user terminal.

9 Claims, 7 Drawing Sheets

(51) Int. Cl.
*G16H 10/60* (2018.01)
*G06F 9/54* (2006.01)

(56) References Cited

FOREIGN PATENT DOCUMENTS

| KR | 1020160144570 A | 12/2016 |
|----|-----------------|---------|
| KR | 1020190059578 A | 5/2019 |
| KR | 102097622 B1 | 4/2020 |
| KR | 102110388 B1 | 5/2020 |
| KR | 101561242 B1 | 7/2020 |

* cited by examiner

CLOUD-BASED API SPEC MANAGEMENT METHOD FOR SIMULTANEOUSLY INTERCONNECTING PLURALITIES OF HOSPITAL SERVERS AND CONSORTIUM SERVERS

CROSS-REFERENCE TO RELATED APPLICATIONS

This application is a national stage of the PCT application No. PCT/KR2021/001956 that was filed on Feb. 16, 2021 claiming the priority of Korean Patent Application No. 10-2020-0074341 filed on Jun. 18, 2020 in the Korean Intellectual Property Office, the disclosure of which is incorporated herein by reference.

BACKGROUND OF THE INVENTION

Technical Field

The embodiments of the invention relates to a cloud-based API management method for simultaneously interworking multiple hospital servers and consortium servers, and in particular, to a cloud-based API specification management method which provides an integrated interface from a cloud server by simultaneously interworking multiple hospital servers and consortium servers.

Background Art

Recently, untact medical services are attracting attention around the world so as to prevent the spread of infectious diseases and infection in medical institutions. In particular, face-to-face contact in hospitals, consortium companies related to the hospitals such as kiosk companies, and service providers are requesting mobile services, but there is a difficulty in interworking because databases of multiple hospitals and consortium companies are different from each other. Furthermore, there is a problem that a source is required for each hospital to develop services due to different hospital systems. The hospitals require various types of interfaces to access data and service data for managing the hospital systems, such as EMR, LIS, OCS, PACS, MIS, HIS, or ERP, which are existing different legacy hospital systems. In addition, since there are various types of middleware, corresponding data interfaces are required. An interface method requires a data interwork system having various N structures such as API, HTTPS, web service, socket communication, HTTP (SOAP), or procedure call.

As the related art, Korean Patent No. 10-1989474 entitled "Cloud-based electronic prescription transmission system and method" has been proposed. This is the registered patent of the applicant, which discloses a system for converting prescription information according to a unique API through an API builder unit disposed in a hospital server and then transmitting an electronic prescription based on the converted information.

In the related art, the API builder unit disposed in the hospital server extracts patient information and prescription information from an EMR DB and then converts the prescription information and the patient information using the API. That is, a data source may be generated in the API builder, may be easily written through SQL query writing guide, may be converted into standard data through the API builder, and then may be repeatedly verified. Thereby, it is possible to standardize pieces of data developed in a development language different from data between heterogeneous DBMS. However, in such a system, the API builder is installed in each of different hospital servers or medical institution servers, thus causing a difficulty in integrated management. Further, since the API is manually managed, the matching of data is not checked.

SUMMARY

Technical Problem

An aspect of the embodiments of the invention provides a cloud-based API specification management method for simultaneously interworking multiple hospital servers and consortium servers, in which a cloud server provides a predefined API to the hospital servers and the consortium servers, so that services including a medical treatment service and an indemnity-health insurance claim can be conveniently provided through the cloud server without the necessity of directly accessing to the hospital servers and the consortium servers.

Technical Solution

According to an embodiment of the present disclosure, a cloud-based API specification management method for simultaneously interworking multiple hospital servers and consortium servers includes a step where a user terminal selects at least one service from patient number inquiry, medical appointment, pharmaceutical preparation, payment and indemnity-health insurance claim services in a dedicated application, a step where the user terminal transmits patient-specific information and a service selection result to the cloud server, a step where the cloud server simultaneously requests patient data from the multiple hospital servers based on the patient-specific information, a step where the cloud server receives the patient data from the multiple hospital servers, a step where the cloud server merges multiple pieces of patient data, a step where the cloud server simultaneously requests services from the multiple consortium servers in response to the service selected by the user terminal, and a step where the multiple consortium servers provide a requested service using the API.

Advantageous Effects

According to the embodiments of the invention, there is an effect that a Private API becomes an open API of a hospital to serve as the standard of a rear eco-system. It is possible to develop services with a single source even in each of hospital systems which are different from each other. Furthermore, it is possible to simultaneously interwork multiple hospital servers and multiple consortium servers, so that integrated management of patient data is possible. Furthermore, it is possible to provide an integrated interface to patients by extracting and merging patient data of multiple hospital servers and consortium servers.

Furthermore, the security of hospital servers or consortium servers is enhanced because a user terminal does not directly access the servers. This can be applied to tens of thousands of hospitals and consortiums, so that its expandability is high.

Furthermore, it is possible to provide a mobile service through a single patient app regardless of various data formats of hospitals and consortiums. In addition, the hospitals and consortiums can use a created data structure to provide data as an open API function without an additional development task through an API engine in other apps requiring the same service.

DESCRIPTION OF EXEMPLARY EMBODIMENTS

Specific structural or functional descriptions in the embodiments of the present disclosure introduced in this specification or application are only for description of the embodiments of the present disclosure. The descriptions should not be construed as being limited to the embodiments described in the specification.

Since the present disclosure may be embodied in many different forms, various embodiments are illustrated in the drawings and described in detail herein. However, it is to be understood that the present description is not intended to limit the present disclosure to those exemplary embodiments, and the present disclosure is intended to cover not only the exemplary embodiments, but also various alternatives, modifications, equivalents and other embodiments that fall within the spirit and scope of the present disclosure.

The terminology used herein is for the purpose of describing particular embodiments only and is not intended to be limiting. In the present disclosure, the singular forms are intended to include the plural forms as well, unless the context clearly indicates otherwise. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Hereinafter, exemplary embodiments of the present disclosure will be described in detail with reference to the accompanying drawings. The term "API specification" refers to definitions and rules for easily describing and expressing the API. This makes the API to be more easily understood, and may be automatically generated with codes of various programming languages.

Figure 1:
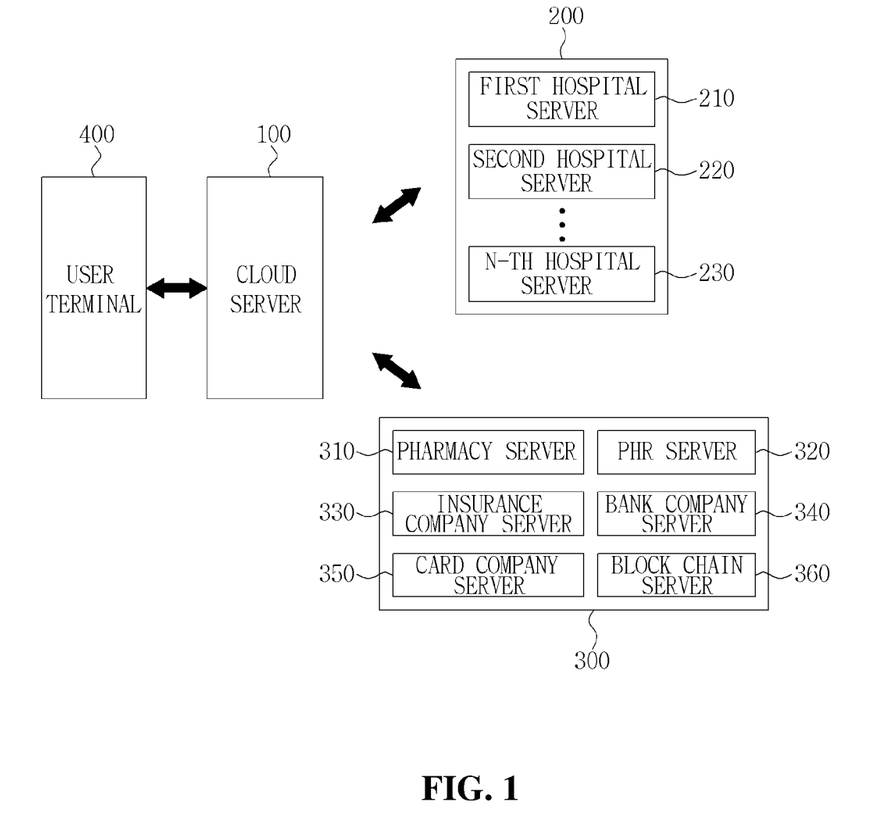
FIG. 1 is a diagram illustrating the configuration of a cloud-based API specification management system for simultaneously interworking multiple hospital servers and consortium servers, according to an embodiment of the present disclosure.

FIG. 1 is a diagram illustrating the configuration of a cloud-based API specification management system for simultaneously interworking multiple hospital servers, according to an embodiment of the present disclosure.

Referring to FIG. 1, the API management system 10 includes a cloud server 100, multiple hospital servers 200, multiple consortium servers 300, and a user terminal 400. The cloud server 100 may generate an API provided to the multiple hospital servers 200 and the multiple consortium servers 300, and may perform the function of managing the API. The multiple consortium server 300 may include a pharmacy server 310, a PHR server 320, an insurance company server 330, a bank company server 340, a card company server 350, and a block chain server 360. The cloud server 100 may provide a predefined API to the hospital server and the consortium server, so that a service may be conveniently provided through the cloud server without the necessity of directly accessing to the hospital server and the consortium server when the user terminal 400 requests the service such as medical treatment service and a claim on indemnity health insurance.

Figure 2:
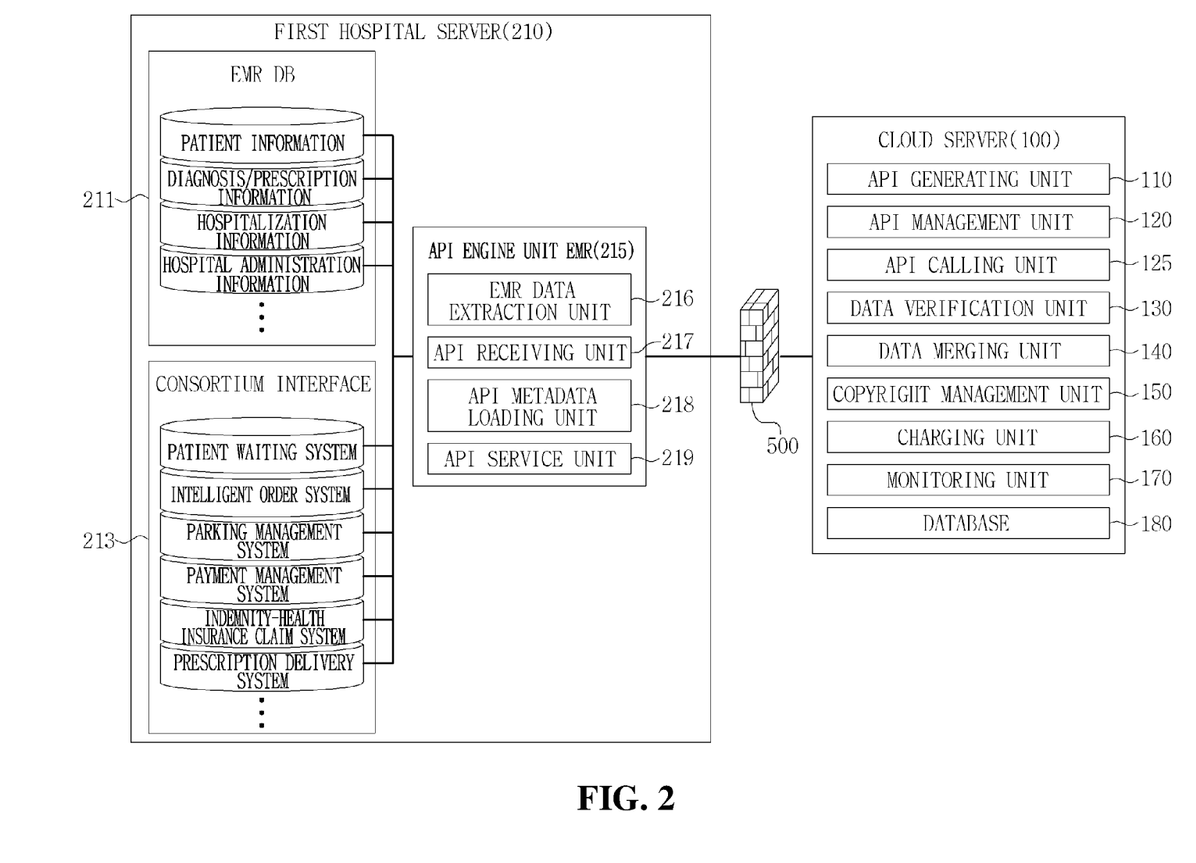
FIG. 2 is a diagram illustrating the configuration of a cloud server and a hospital server, according to an embodiment of the present disclosure.

FIG. 2 is a diagram illustrating the configuration of the cloud server and the hospital server, according to an embodiment of the present disclosure.

Referring to FIG. 2, the cloud server 100 includes an API generating unit 110, an API management unit 120, an API calling unit 125, a data verification unit 130, a data merging unit 140, a copyright management unit 150, a charging unit 160, a monitoring unit 170, and a database 180.

The API generating unit 110 may generate the predefined API for providing an integrated interface of the hospital servers and the consortium servers. This API may be the API for standardizing database information of the hospital servers and the consortium servers. The API generating unit 110 may define a data source, and may register SQL and procedures. Furthermore, the API generating unit 110 may register middleware access information and call routes, and may register web service access information and an URL.

When the API management unit 120 receives a service call from the user terminal, it may call the API matching with a corresponding service to simultaneously provide patient number inquiry, medical appointment, payment, and indemnity-health insurance claim services to the multiple hospital servers and consortium servers. The API management unit 120 may check input and output errors through an API constraint condition management function. The API management unit 120 may monitor the status of the API service of each hospital server and consortium server, version information, memory usage, disk usage, CPU usage of the server, etc. The API management unit 120 may encode sensitive information and may store it in the database. The API management unit 120 may manage a domain of the API. The API management unit 120 may add metadata for automatic distribution, when the API specification managed in the metadata is changed. That is, a standardized mapping definition may be written, and a mapping sample example may be used in a standardized prototype template according to a processing method, thus selectively registering a programmed processor and extracted data to generate a standardized source loading program.

The API calling unit 125 is implemented to automatically call the API, and is operated to simultaneously make calls in parallel with the multiple hospital servers and consortium servers.

The data verification unit 130 may perform an error test of the generated API. If there is error data, the data and the API may be stored and distributed after the data is corrected.

The data merging unit 140 may receive and merge patient data from the multiple hospital servers. When a patient uses several hospitals, it is possible to receive and merge the patient data from each hospital server, thus enhancing convenience.

The copyright management unit 150 may manage copyright through a classification system which may be identified for each hospital server. The copyright management unit 150 may manage a program source and a version, and may set a management-number classification system for each function or architecture, thus providing an interface guideline for each function.

The charging unit 160 may perform charging when the API is used in the consortium server after checking the predefined API of the hospital server. The charging unit 160 may measure the API usage of the consortium server, and may reflect use status/statistics for each group.

The monitoring unit 170 may monitor interworking of the multiple hospital servers and consortium servers. The database 180 may store an API tool.

That is, the predefined API specification may be registered as the metadata and then the API may be provided to the hospital server. Conventionally, the API specification managed by Excel and confluence is registered as the metadata, the API specification suitable for each hospital server is selected, and then is automatically distributed to the API engine of each hospital server.

Furthermore, an app service for patients may be quickly built by managing the API metadata in the cloud server 100 to interwork the cloud server and the hospital server through a firewall in the form of standardized data. To be more specific, when providing the app service for patients, a content menu for patients may be defined, and a data structure for a content menu screen may be defined in the form of an open API so as to apply the data structure for the content menu to all hospitals. If each hospital extracts the data in SQL, JSON, XML, and specialized data form, the API may interwork with the cloud server in the form of standardized data, thus quickly building the app service for patients and providing services. This enables all hospitals to perform mobile services with the same single app for patients. The hospitals may provide data with the open API function without additional development task through the API even in other apps which require the same service, using the data structure which is previously made. In addition, an URL interwork to a sample screen may be provided for each API, so that a hospital staff may write more easily.

Furthermore, the cloud server 100 may provide virtual data management for supporting developers and testers, and may check actual data which supports operators and operations testers for real service support. In a step of implementing multiple data interfaces by one business logic, it is possible to provide an overall connection method which provides a step of requesting development/test/verification, a step of distributing an application, and development and operation of a new service. The cloud server 100 may provide the overall connection method while sticking to an internal security policy based on a hospital's security and medical law, in a step where one business logic is interworked with the multiple data interfaces. The cloud server 100 may provide a connection method for constructing and interworking an infrastructure for performing the interface of multiple hospitals. Here, a basic API server internal system may be configured as a dedicated VPN. After the cloud server 100 confirms the standardized API of the hospital server, it may provide a method where a consortium group observes the corresponding contents and guides an interface in the form of the open API.

A first hospital server 210 includes an EMR DB 211, a consortium interface 213, and an API engine unit 215. The EMR DB 211 may store patient information, diagnosis/prescription information, hospitalization information, hospital administration information, etc. The consortium interface 213 includes a patient waiting system, an intelligent order system, a parking management system, a payment management system, an indemnity-health insurance claim system, a prescription delivery system, etc. The configuration of the EMR DB 211 and the consortium interface 213 is illustrated by way of example, but is not limited thereto.

The API engine unit 215 may extract data from the EMR DB 211. The API engine unit 215 may receive and load the Application Programming Interface (API) for each hospital server received from the cloud server, and may load API metadata from the cloud server, thus performing the API service. The API engine unit 225 is a development tool which accesses to the hospital legacy in various environments to support the API, as a middleware which is installed in the hospital server to connect a mobile service and the hospital server. That is, this is installed in the hospital server to develop a Restful API for interworking with various systems in the hospital as well as app services for patients and be used as a gateway server. The API engine unit 215 includes an EMR data extraction unit 216, an API receiving unit 217, an API metadata loading unit 218, and an API service unit 219. The EMR data extraction unit 216 may extract data from the EMR DB 211. The API receiving unit 217 may receive the API for each hospital server generated from the cloud server. The API metadata loading unit 218 may load the API metadata from the cloud server. The API service unit 219 may drive the API service based on the API metadata.

Figure 3:
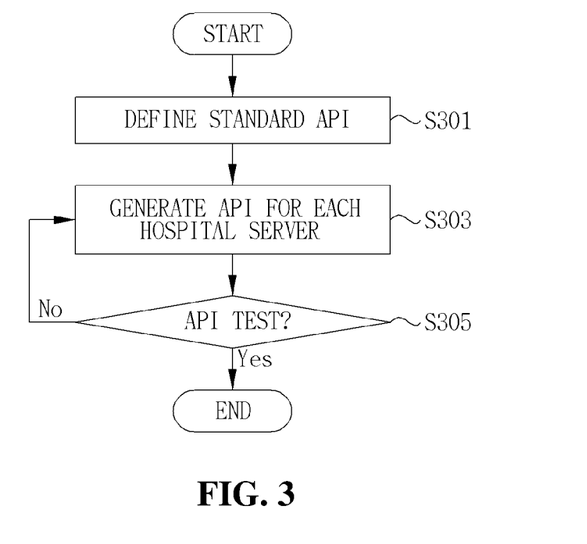
FIG. 3 is a flowchart illustrating an operating method of an API generating unit of a cloud server, according to an embodiment of the present disclosure.

FIG. 3 is a flowchart illustrating an operating method of the API generating unit of the cloud server, according to an embodiment of the present disclosure. Referring to FIG. 3, the cloud server defines a standard API (S301). Subsequently, the cloud server generates the API for each hospital server or consortium server (S303). The generated API is tested (S305). If there is no error, data and the API may be stored and distributed. If there is an error, data may be corrected and then the data and the API may be stored and distributed.

Figure 4:
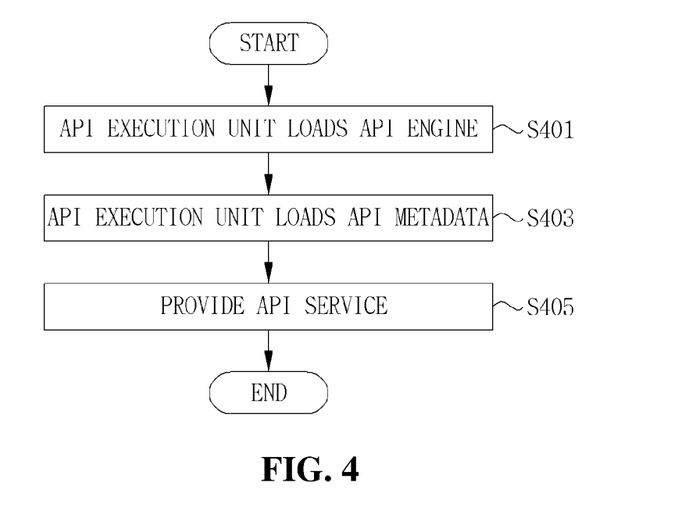
FIG. 4 is a flowchart illustrating an operating method of an API engine unit of a hospital server, according to an embodiment of the present disclosure.

FIG. 4 is a flowchart illustrating an operating method of the API engine unit of the hospital server, according to an embodiment of the present disclosure.

Referring to FIG. 4, the API engine unit of the hospital server starts the API engine (S401). Subsequently, an API execution unit loads the API metadata from the cloud server (S403). The API service is driven based on the loaded API metadata (S405).

Figure 5:
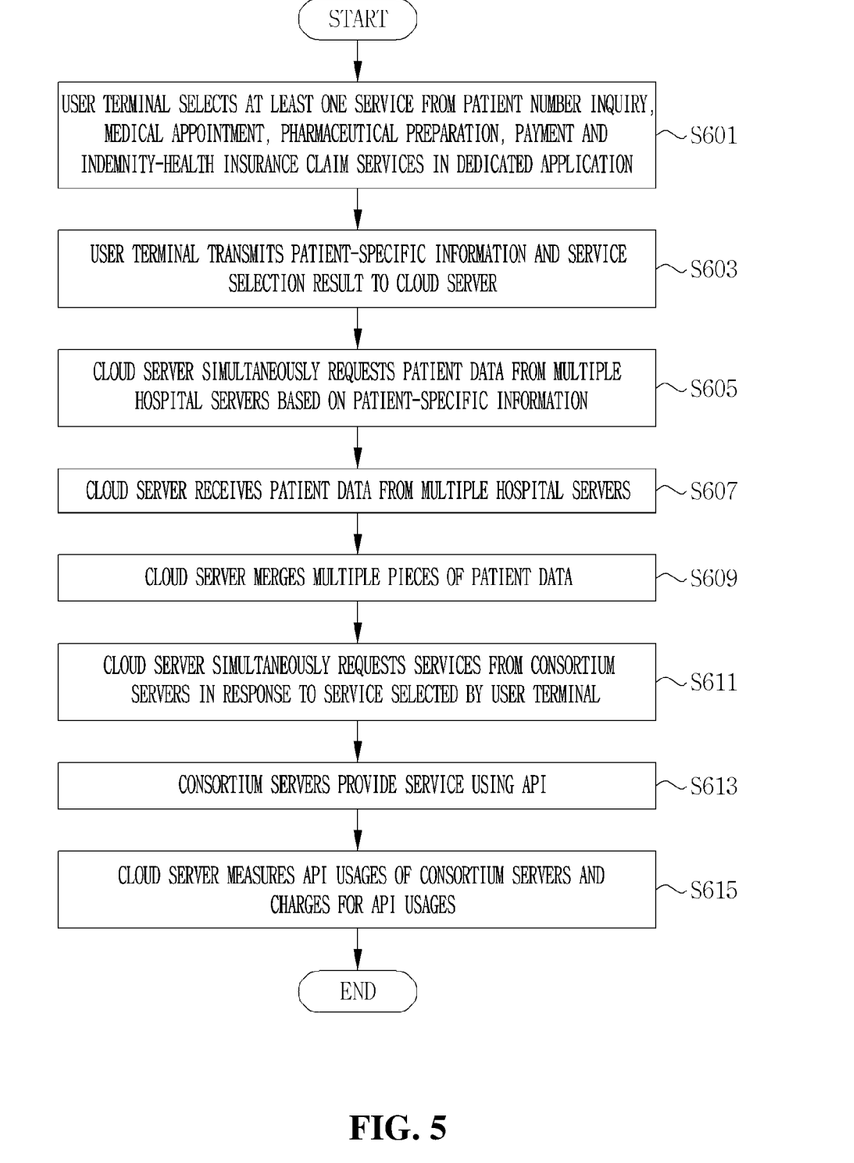
FIG. 5 is a flowchart illustrating a cloud-based API specification management method for simultaneously interworking multiple hospital servers and consortium servers, according to an embodiment of the present disclosure.

FIG. 5 is a flowchart illustrating a cloud-based API specification management method for simultaneously interworking the multiple hospital servers, according to an embodiment of the present disclosure.

Referring to FIG. 5, the user terminal 400 selects at least one service from patient number inquiry, medical appointment, pharmaceutical preparation, payment and indemnity-health insurance claim services in a dedicated application (S601). The user terminal transmits patient-specific information and a service selection result to the cloud server (S603). The cloud server simultaneously requests patient data from the multiple hospital servers based on the patient-specific information (S605). The cloud server receives the patient data from the multiple hospital servers (S607). The cloud server merges multiple pieces of patient data (S609). The cloud server simultaneously requests services from the multiple consortium servers in response to the service selected by the user terminal (S611). The consortium servers provide a service using the API (S613). The cloud server measures the API usages of the consortium servers and then charges for the API usages (S615).

Figure 6:
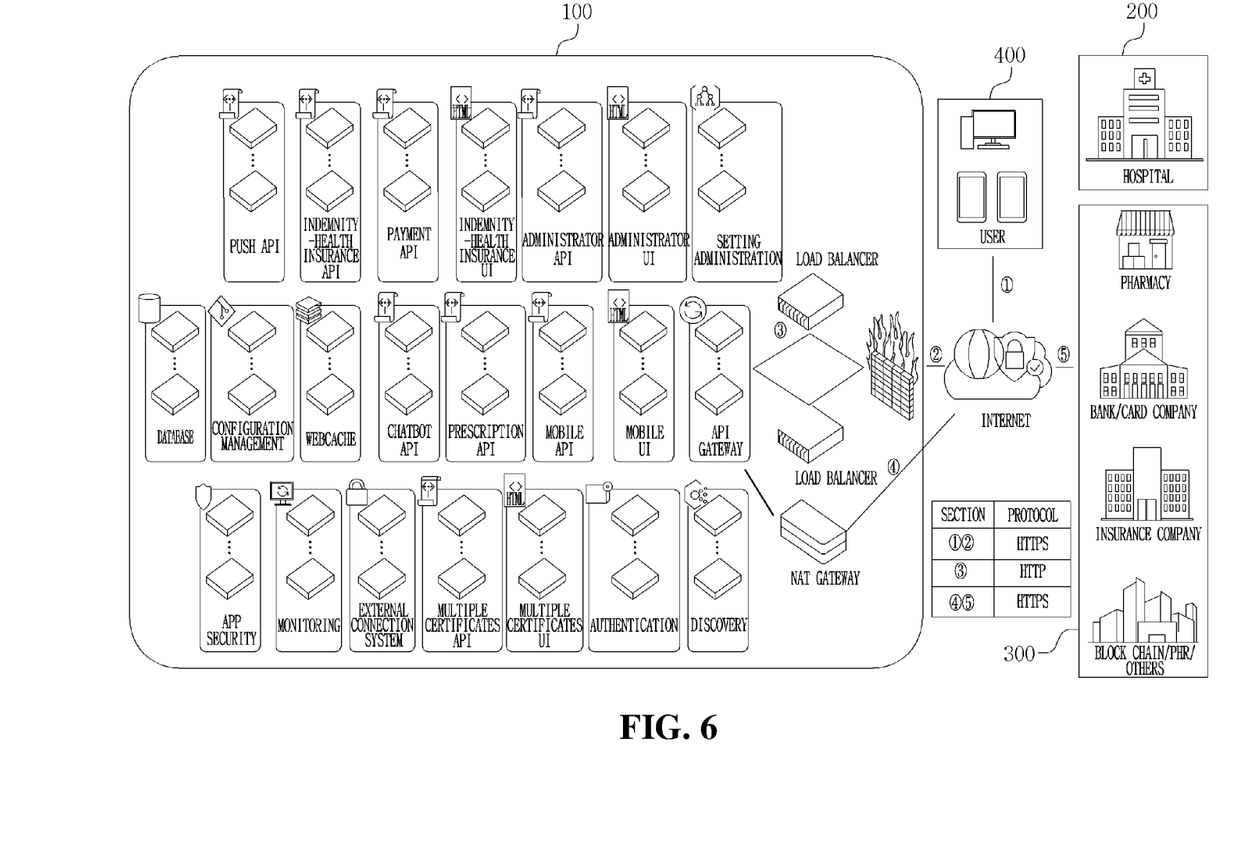
FIG. 6 is a conceptual diagram illustrating a communication protocol of a cloud-based API management system, according to an embodiment of the present disclosure.

FIG. 6 is a conceptual diagram illustrating a communication protocol of the cloud-based API management system, according to an embodiment of the present disclosure. The user terminal 400 and an Internet communication network, the cloud server 100 and an Internet communication network, the hospital server and the consortium server and the Internet communication network use a HTTPS security protocol, and a HTTP protocol is used between a load balancer and the firewall in the cloud server.

Figure 7:
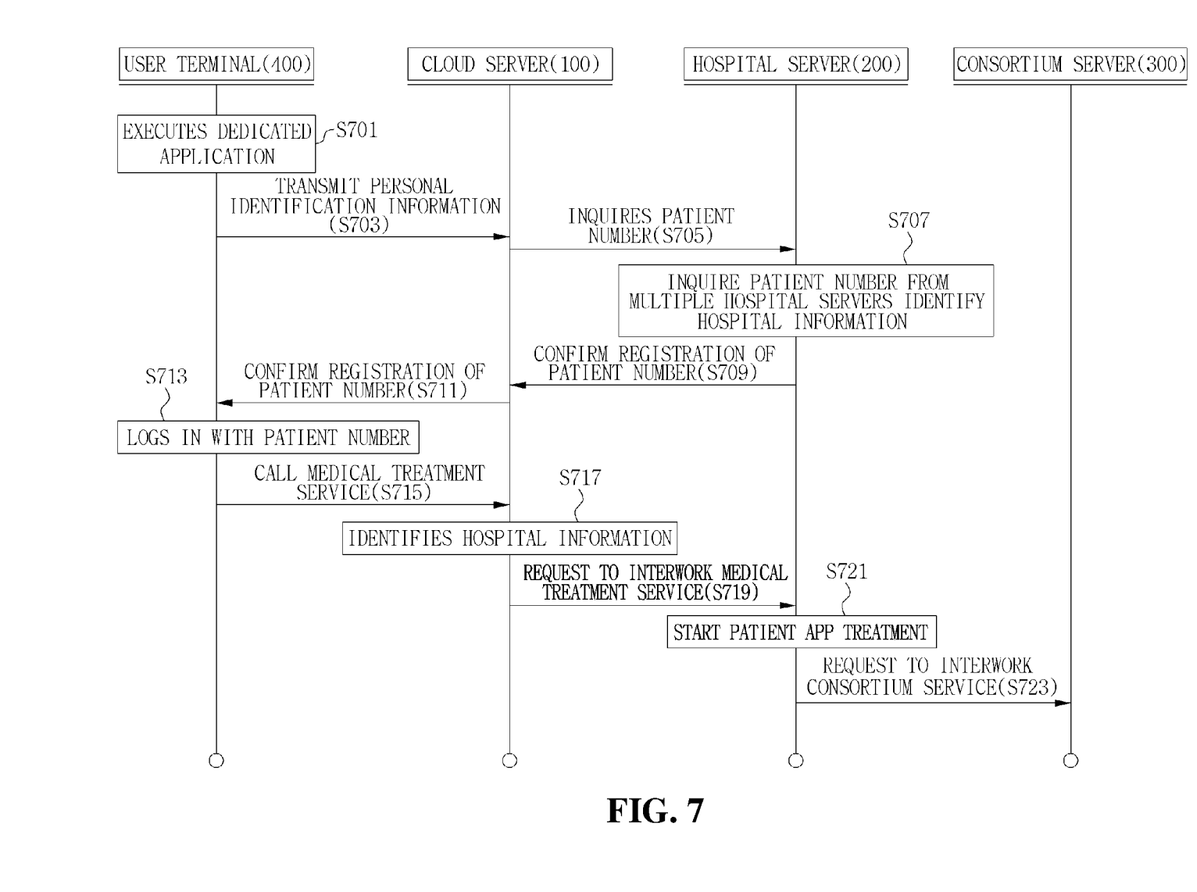
FIG. 7 is a flowchart illustrating a cloud-based API specification management method for simultaneously interworking multiple hospital servers and consortium servers, according to an embodiment of the present disclosure.

FIG. 7 is a flowchart illustrating a cloud-based API specification management method for simultaneously interworking multiple hospital servers and consortium servers, according to an embodiment of the present disclosure.

Referring to FIG. 7, when the user terminal 400 executes a dedicated application (S701) to input personal identification information (S703), the cloud server 100 simultaneously inquires the patient number from the multiple hospital servers 200 (S705).

When the multiple hospital servers 200 inquire the patient number (S707) and the cloud server 100 confirms whether the patient number is registered in at least one hospital server among the multiple hospital servers 200, the registration confirmation of the patient number is transmitted to the cloud server 100 (S709), and the registration of the patient number is transmitted to the user terminal 400 (S711).

The user terminal 400 logs in with the patient number (S713), and the cloud server 100 identifies hospital information (S717). When the cloud server 100 calls the medical treatment service, it requests the hospital server 200 to interwork the medical treatment service (S719). The hospital server 200 starts patient app treatment (S721), and requests the consortium server 300 to interwork the consortium service (S723).

Figure 8:
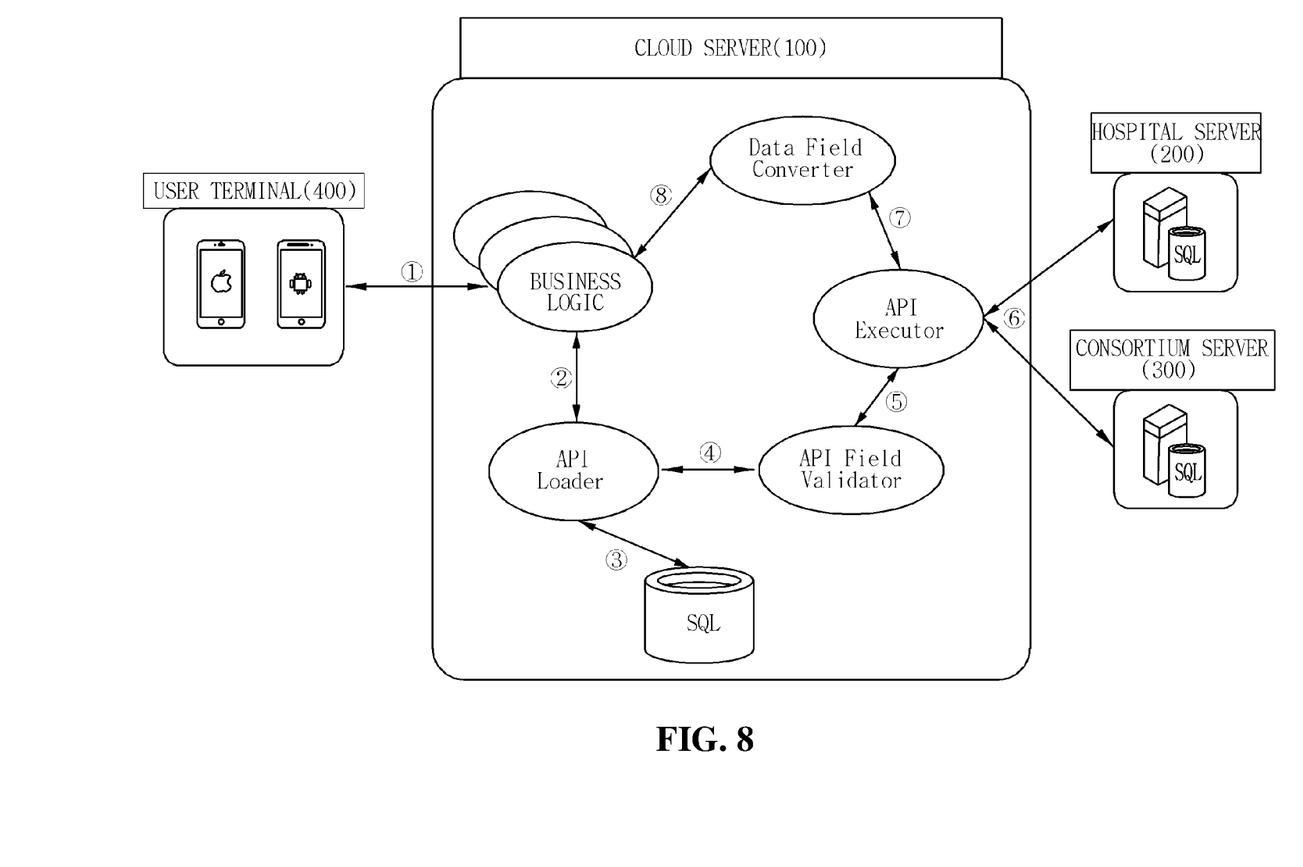
FIG. 8 is a flowchart illustrating an architectural change of a cloud-based API call for simultaneously interworking multiple hospital servers and consortium servers, according to an embodiment of the present disclosure.

FIG. 8 is a flowchart illustrating an architectural change of a cloud-based API call for simultaneously interworking the multiple hospital servers and consortium servers, according to an embodiment of the present disclosure.

Referring to FIG. 8, the user terminal 400 executes the dedicated application, executes the business logic of the cloud server 100 to request data, calls the standard API through an API loader, and inquires API mapping by the API meta-management of the cloud server. After testing API transmission data through an API field validator and interworking the multiple hospital servers and consortium servers to call mapping API, field conversion to the standard API is executed through an API executor and then the business logic and conversion data are returned to provide a service. The matching of data exchanged through the API is checked.

Although the present disclosure was described with reference to specific embodiments shown in the drawings, it is apparent to those skilled in the art that the present disclosure may be changed and modified in various ways. Therefore, the technical scope of the present disclosure should be determined by the appended claims.

What is claimed is:

1. A cloud-based Application Programming Interface (API) management system for simultaneously interworking multiple hospital servers and consortium servers, the system comprising:
   a cloud server, multiple hospital servers, multiple consortium servers, and a user terminal,
   wherein the cloud server comprises:
   an API generating unit configured to generate a predefined API for providing an integrated interface of the hospital servers and the consortium servers;
   an API management unit configured to call an API matching with a corresponding service to simultaneously provide at least one service of patient number inquiry, medical appointment, payment, and indemnity-health insurance claim services to the multiple hospital servers and consortium servers when the API management unit receives a service call from the user terminal;
   a data verification unit configured to perform an error test of the generated API; and
   a data merging unit configured to receive and merge patient data from the multiple hospital servers,
   wherein the cloud server provides the predefined API to the hospital server and/or the consortium server, such that, by using the predefined API, the at least one service is directly provided through the cloud server with substituting a direct access to the hospital server and/or the consortium server when the user terminal requests the least one service.

2. The cloud-based API management system of claim 1, further comprising:
   a charging unit configured to measure API usage of the consortium server and to reflect use status/statistics for each group, thus charging for the API usage, when the consortium server uses the API after checking the predefined API of the hospital server.

3. The cloud-based API management system of claim 1, wherein
   the hospital server comprises an EMR DB and an API engine unit, and
   the API engine unit extracts data from the EMR DB, receives and loads the predefined API for each hospital server received from the cloud server, and loads API metadata from the cloud server, thus performing an API service.

4. The cloud-based API management system of claim 1, wherein the predefined API is configured to standardize a database information of the hospital servers and/or the consortium servers.

5. The cloud-based API management system of claim 1, wherein the API generating unit is further configured to define a data source to register Structured Query Language (SQL) and SQL procedures.

6. The cloud-based API management system of claim 1, wherein the API generating unit is further configured to register a middleware access information, call routes, a web service access information and a Uniform Resource Locator (URL).

7. The cloud-based API management system of claim 1, wherein the API management unit is further configured to check input and output errors of the predefined API, monitor a status of API services of the hospital server and/or the consortium server, a version information of the hospital server and/or the consortium server, a memory usage of the hospital server and/or the consortium server, a disk usage of the hospital server and/or the consortium server, a CPU usage of the hospital server and/or the consortium server.

8. The cloud-based API management system of claim 1, wherein the API management unit is further configured to encode a sensitive information and store the sensitive information in a database.

9. The cloud-based API management system of claim 1, wherein the API management unit is further configured to manage a domain of the predefined API, update metadata for automatic distribution in response to a change of an API specification in the metadata, such that a standardized mapping definition is written in the API specification, and a mapping sample is used in a standardized prototype template, with selectively registering a programmed processor and an extracted data to generate a standardized source loading program.

* * * * *